(12) United States Patent
Lewallen

(10) Patent No.: US 6,887,278 B2
(45) Date of Patent: May 3, 2005

(54) PROSTHETIC IMPLANT HAVING SEGMENTED FLEXIBLE STEM

(75) Inventor: David G. Lewallen, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 155 days.

(21) Appl. No.: 10/287,113

(22) Filed: Nov. 4, 2002

(65) Prior Publication Data

US 2004/0088056 A1 May 6, 2004

(51) Int. Cl.[7] ................................................. A61F 2/32
(52) U.S. Cl. ................................. 623/22.11; 623/23.17; 623/23.24
(58) Field of Search .................. 623/22.11, 22.12, 623/22.14, 22.4, 22.41, 23.15, 23.17, 23.18, 23.36, 23.3, 23.24, 23.25

(56) References Cited

U.S. PATENT DOCUMENTS

| | | | | |
|---|---|---|---|---|
| 2,719,522 A | * | 10/1955 | Hudack | 623/23.15 |
| 3,067,740 A | | 12/1962 | Harboush | |
| 3,781,917 A | * | 1/1974 | Mathys | 623/23.27 |
| 3,818,512 A | * | 6/1974 | Shersher | 623/22.15 |
| 3,987,499 A | | 10/1976 | Scharbach et al. | |
| 3,996,625 A | | 12/1976 | Noiles | |
| 4,059,854 A | * | 11/1977 | Laure | 623/23.16 |
| 4,146,936 A | * | 4/1979 | Aoyagi et al. | 623/23.57 |
| 4,292,695 A | | 10/1981 | Koeneman | |
| 4,314,381 A | * | 2/1982 | Koeneman | 623/23.17 |
| 4,355,428 A | * | 10/1982 | Deloison et al. | 623/23.5 |
| 4,404,691 A | | 9/1983 | Buning et al. | |
| 4,407,022 A | * | 10/1983 | Heimke et al. | 623/23.24 |
| 4,531,915 A | * | 7/1985 | Tatum, Jr. | 433/173 |
| 4,668,290 A | | 5/1987 | Wang et al. | |
| 4,693,724 A | * | 9/1987 | Rhenter et al. | 623/22.44 |
| 4,808,186 A | | 2/1989 | Smith | |
| 4,878,919 A | * | 11/1989 | Pavlansky et al. | 623/23.18 |
| 4,921,501 A | | 5/1990 | Giacometti | |
| 4,986,834 A | * | 1/1991 | Smith et al. | 623/23.32 |
| 4,997,444 A | | 3/1991 | Farling | |
| 5,007,931 A | | 4/1991 | Smith | |
| 5,092,899 A | | 3/1992 | Forte | |
| 5,108,450 A | | 4/1992 | Horber et al. | |
| 5,181,928 A | | 1/1993 | Bolesky et al. | |
| 5,316,550 A | | 5/1994 | Forte | |
| 5,336,265 A | | 8/1994 | Serbousek et al. | |
| 5,462,563 A | | 10/1995 | Shearer et al. | |
| 5,507,830 A | | 4/1996 | DeMane et al. | |
| 5,509,935 A | | 4/1996 | Fosco et al. | |
| 5,591,233 A | | 1/1997 | Kelman et al. | |
| 5,702,482 A | | 12/1997 | Thongpreda et al. | |
| 5,725,586 A | | 3/1998 | Sommerich | |
| 5,824,097 A | | 10/1998 | Gabriel et al. | |
| 6,071,311 A | | 6/2000 | O'Neil et al. | |
| 6,312,473 B1 | * | 11/2001 | Oshida | 623/23.55 |

FOREIGN PATENT DOCUMENTS

| | | |
|---|---|---|
| GB | 2223172 A | 4/1990 |
| WO | WO 86/06954 A1 | 12/1986 |
| WO | WO 89/01321 A1 | 2/1989 |

* cited by examiner

*Primary Examiner*—Pedro Philogene
*Assistant Examiner*—D. Austin Bonderer
(74) *Attorney, Agent, or Firm*—Quarles & Brady LLP

(57) ABSTRACT

A prosthetic implant having a fixation stem with varying stiffness is disclosed. The stem comprises an elongated core and segments extending outward from the core. The segments are spaced apart so as to define transverse grooves surrounding the core between adjacent segments. The longitudinal length of the grooves, and the materials used for the core and the segments are selected such that the stiffness of the stem varies from the proximal end to the distal end. Typically, the stiffness of the stem will be lower at the distal end such that the distal end of the stem bears less force when loaded and thereby transfers more load to the proximal end of the stem, which has a higher stiffness. As a result, stress shielding, in which the load bypasses the proximal end of the stem, is minimized and bone resorption adjacent the proximal end of the stem is decreased.

8 Claims, 3 Drawing Sheets

PROSTHETIC IMPLANT HAVING SEGMENTED FLEXIBLE STEM

CROSS-REFERENCE TO RELATED APPLICATIONS

Not Applicable.

STATEMENT REGARDING FEDERALLY SPONSORED RESEARCH

Not Applicable.

BACKGROUND OF THE INVENTION

1. Field of the Invention

This invention relates to prosthetic implants having a fixation stem, and in particular relates to a prosthetic implant having a fixation stem with decreased or varying stiffness such that the problems associated with stress shielding are reduced.

2. Description of the Related Art

For many years now, prostheses have been implanted in the human body to repair or reconstruct all or part of an articulating skeletal joint, such as the hip joint. The hip joint includes the femur and the pelvis, each of which has a surface for articulation against an adjacent articulation surface of the other bone. The femur has a head having a convex, generally spherically contoured articulation surface. The pelvis includes an acetabulum having a concave, generally spherically contoured articulation surface. The articulation surfaces of the femur and the pelvis form a ball-and-socket type joint.

One or both of the articulation surfaces of the hip joint may fail to perform properly, requiring the defective natural articulation surface to be replaced with a prosthetic articulation surface. In an artificial hip joint, a femoral implant can be used to replace the natural head and articulating surface of the femur, and an acetabular cup can be used to replace the natural socket and articulating surface of the acetabulum of the pelvis. The natural or artificial femoral head articulates directly against the natural acetabulum or the artificial acetabular cup.

A femoral implant may be affixed to the femur using bone cements. While bone cements provide the initial fixation necessary for healing following surgery, bone cements often result in a very stiff overall structure, are prone to loosening with time, and can provoke tissue reactions. Because of the disadvantages associated with the use of bone cements, "cementless" or "press fit" femoral implants have been developed. One well known "cementless" or "press fit" femoral implant includes a stem. The femoral implant stem "press-fits" into the intramedullary canal of the femur to hold the femoral implant rigidly in the femur.

A recognized problem with the use of an interference fit (press-fit) femoral implant stem is that transfer of stress from the femoral implant to the femur is abnormal. Instead of a normal loading of the femur primarily at the end of the femur near the joint surface, the femur is loaded more distally where the stem of the implant contacts the femur. This results in a phenomenon called "stress shielding" in which the load (i.e., stress) bypasses or "unloads" the end of the joint surface portion of the femur. As a result, the joint surface portion of the femur undergoes resorption, (i.e., the femur retreats from its tight fit around the implant stem) thereby introducing some "play" into the fit. This leads to weakening over a period of years, thus creating a potential for fracture or a loosening of the femoral implant within the femur.

It has been reported that one cause of stress shielding is the high bending stiffness of conventional femoral implant stems. In particular, the relatively high mechanical stiffness of the stem portion of metallic femoral implants tends to stress protect (i.e., "unload") the proximal femur which can lead to resorption and loosening of the femoral implant. Because stem stiffness increases exponentially in relation to stem diameter, patients with relatively large intramedullary canals, which require a femoral implant with a large diameter stem for optimal fit, can be particularly susceptible to this phenomenon of "stress shielding". In extreme cases, the proximal femoral bone may resorb to a small fraction of its original mass, possibly causing a loss of support of the implant or implant breakage.

In order to eliminate the stress shielding problems associated with the high mechanical stiffness of the stem portion of metallic femoral implants, it has been proposed to produce a femoral implant having a stem with reduced mechanical stiffness or varying mechanical stiffness along the length of the stem. For example, U.S. Pat. Nos. 5,702,482, 5,509,935, 5,336,265, 5,007,931, 4,921,501 and 4,808,186 disclose femoral implants including a stem with longitudinal slots or channels that serve to decrease the stiffness of the stem. The reduced stiffness of the stem decreases stress shielding. It has also been proposed in U.S. Pat. Nos. 5,725,586, 5,316,550 and 5,092,899 that the stiffness of the stem of a femoral implant can be reduced by hollowing out the interior of the stem.

While each of these patents may provide a solution to the stress shielding problems associated with the high mechanical stiffness of the stem of a femoral implant, these stemmed implants do have certain disadvantages. For instance, implants that include a stem with longitudinal slots may not provide for a snug press fit and may not provide sufficient surface area for bone ingrowth. Also, hollowing out the stem of a femoral implant may only be marginally effective at reducing stress shielding, due to the fact that the centrally located material contributes little to the stiffness of the implant.

Therefore, there is a continuing need for an improved prosthetic implant having a fixation stem with reduced stiffness such that the stress shielding problems associated with the high mechanical stiffness of the stem can be minimized. In particular, there is a need for an improved prosthetic implant having a fixation stem wherein the stiffness at the distal end of the stem is reduced such that the proximal end of the stem may bear more load.

SUMMARY OF THE INVENTION

The foregoing needs are met by a prosthesis according to the invention for implanting into a bone having a cavity. The prosthesis comprises a body and a stem fastened to the body at a proximal end and extending longitudinally away from the body to form a distal end. The stem comprises an elongated core and a plurality of segments extending outward from the core. The core and the segments consist essentially of a microstructurally consistent implant material. The stem has an outer layer that at least partially contacts an inner surface of the cavity of the bone when the prosthesis is implanted into the cavity of the bone.

The segments are spaced apart so as to define transverse grooves surrounding the core between adjacent segments. The longitudinal length of at least one segment is greater than the longitudinal length of each groove and the longitudinal length of at least two transverse grooves varies such that the stiffness of the stem varies from the proximal end to the distal end of the stem. Typically, the stiffness of the stem will be lower at the distal end of the stem such that the distal end of the stem bears less force when loaded and thereby transfers more load to the proximal end of the stem, which has a higher stiffness. As a result, "stress shielding", in which the load bypasses or "unloads" the proximal end of the stem, is minimized and bone resorption adjacent the proximal end of the stem is decreased. At the same time, sufficient surface area is provided on the outer layer of the segments such that the ingrowth of bone tissue is not materially hindered thereby decreasing the possibility of the prosthesis loosening.

In a second aspect of the invention, there is provided a prosthesis for implanting into a bone having a cavity. The prosthesis comprises a body, and a stem fastened to the body at a proximal end and extending longitudinally away from the body to form a distal end. The stem comprises an elongated core and a plurality of tubular segments surrounding and affixed to the core. Each segment has an outer layer that at least partially contacts an inner surface of the cavity of the bone when the prosthesis is implanted into the cavity of the bone, and the segments are spaced apart so as to define a transverse groove surrounding the core between adjacent segments.

At least one segment located adjacent the proximal end of the stem comprises a first material having a first modulus of elasticity, and at least one segment located adjacent the distal end of the stem comprises a second material having a second modulus of elasticity. The first modulus of elasticity is different from the second modulus of elasticity such that the stiffness of the stem varies from the proximal end to the distal end of the stem. Preferably, the first modulus of elasticity is greater than the second modulus of elasticity such that the stiffness of the stem will be lower at the distal end of the stem such that the distal end of the stem bears less force when loaded and thereby transfers more load to the proximal end of the stem, which has a higher stiffness. As a result, "stress shielding" is minimized and bone resorption adjacent the proximal end of the stem is decreased. At the same time, sufficient surface area is provided on the outer layer of the segments such that the ingrowth of bone tissue is not materially hindered thereby decreasing the possibility of the prosthesis loosening.

In a third aspect of the invention, there is provided a prosthesis for implanting into a bone having a cavity. The prosthesis comprises a body, and a stem fastened to the body at a proximal end and extending longitudinally away from the body to form a distal end. The stem comprises an elongated core and a plurality of tubular segments surrounding and affixed to the core. Each segment has an outer layer that at least partially contacts an inner surface of the cavity of the bone when the prosthesis is implanted into the cavity of the bone, and the segments are spaced apart so as to define a transverse groove surrounding the core between adjacent segments.

At least one segment comprises a first metallic material having a first modulus of elasticity, and the core comprises a second metallic material having a second modulus of elasticity. The first modulus of elasticity is greater than the second modulus of elasticity such that the stiffness of the stem varies from the proximal end to the distal end of the stem. As a result, various stress transfer characteristics can be achieved for the stem. At the same time, sufficient surface area is provided on the outer layer of the segments such that the ingrowth of bone tissue is not materially hindered thereby decreasing the possibility of the prosthesis loosening.

It is therefore an advantage of the present invention to provide a prosthetic implant having a fixation stem with reduced or varying stiffness such that the stress shielding problems associated with the high mechanical stiffness of the stem can be minimized.

It is another advantage of the present invention to provide a prosthetic implant having a fixation stem with reduced or varying stiffness wherein the implant transmits loads to the surrounding support bone in a more optimum manner such that stress shielding in minimized.

It is a further advantage of the present invention to provide a prosthetic implant having a fixation stem with reduced stiffness at the distal end of the stem such that unloading of the proximal end of the stem and associated bone resorption are minimized.

It is a yet another advantage of the present invention to provide a prosthetic implant having a fixation stem with reduced or varying stiffness wherein sufficient stem surface area is maintained for the ingrowth of bone tissue thereby decreasing the possibility of the prosthesis loosening.

BRIEF DESCRIPTION OF THE DRAWINGS

These and other features, aspects, and advantages of the present invention will become better understood upon consideration of the following detailed description, appended claims and drawings where:

Figure 1:
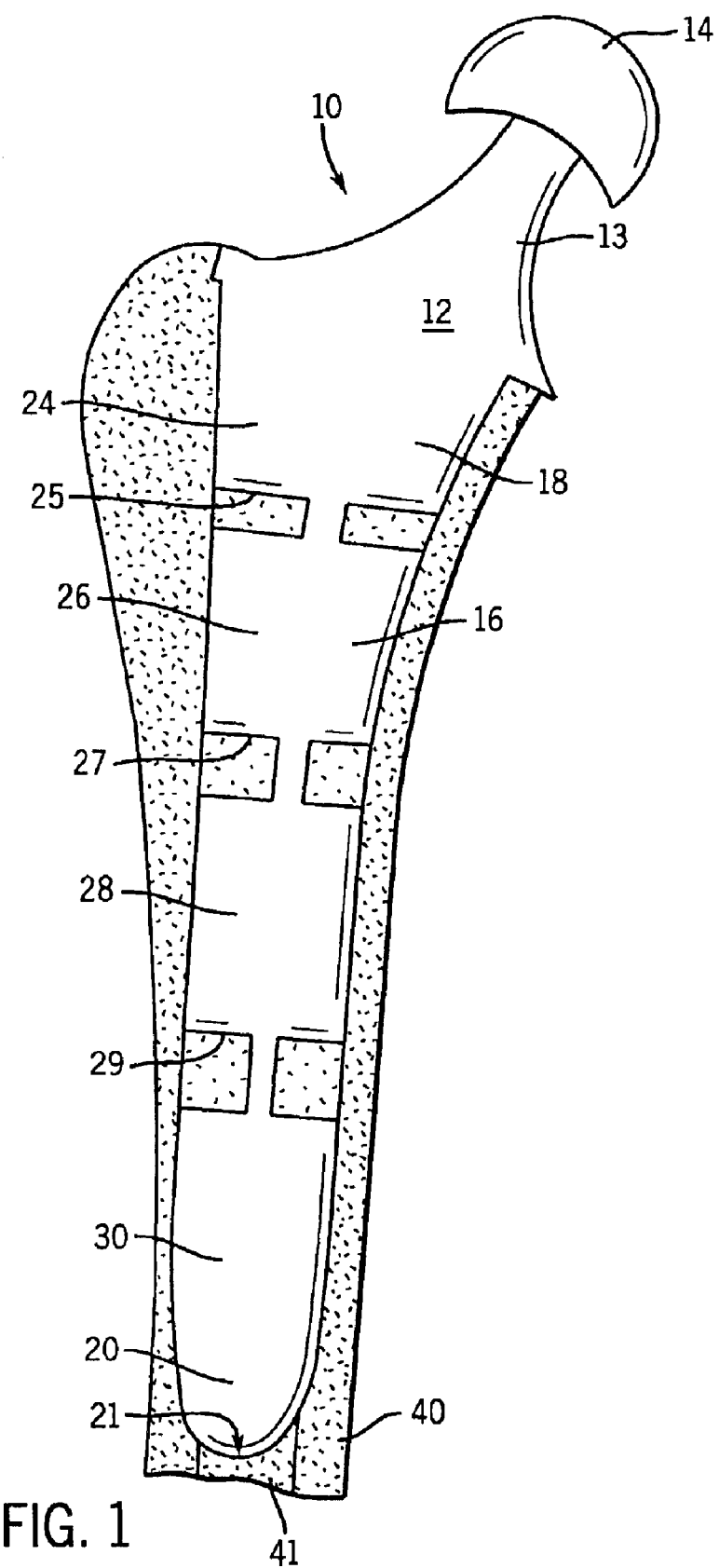
FIG. 1 is a side view of a prosthesis according to the invention implanted in a femur, the femur being shown in cross-section.

It should be understood that the drawings are not necessarily to scale, and details which are not necessary for an understanding of the present invention or which render other details difficult to perceive may have been omitted. Like reference numerals will be used to refer to like or similar parts from Figure to Figure in the following description of the invention.

DETAILED DESCRIPTION OF THE INVENTION

The present invention is directed to a flexible prosthesis for implanting into a bone having a cavity. The prosthesis illustrated and described herein is a femoral prosthesis component of an artificial hip joint in which the femoral prosthesis is implanted in the femoral medullary canal. However, it should be understood that the methods and prostheses according to the invention can be used in the repair of any bone or in connection with the implantation of prosthetic devices in any bone in the body, adjacent to or remote from any joint, including without limitation the hip, knee and spinal joints. Further, the methods and prostheses according to the invention can be used in primary surgery, in which a prosthesis is being used to reconstruct a joint for the first time, as well as in revision surgery in which a previously-implanted prosthesis is being replaced with another prosthesis. Press fit, cement or other fixation techniques can be employed in conjunction with the methods and prostheses according to the invention.

Referring first to FIG. 1, there is shown a femoral prosthesis 10 according to the invention that may be implanted in a resected femur as part of a hip replacement procedure. The prosthesis 10 includes a body 12 having a neck portion 13 and a femoral head 14. The femoral head 14 is received in an acetabular component (not shown) that is mounted in a patient's pelvis as is well known in the art. Longitudinally extending away from and fastened to the body 12 of the prosthesis 10 is a stem 16 that is inserted within the intramedullary canal 41 of the femur 40. The stem 16 has a proximal end 18 and a distal end 20.

Figure 2:
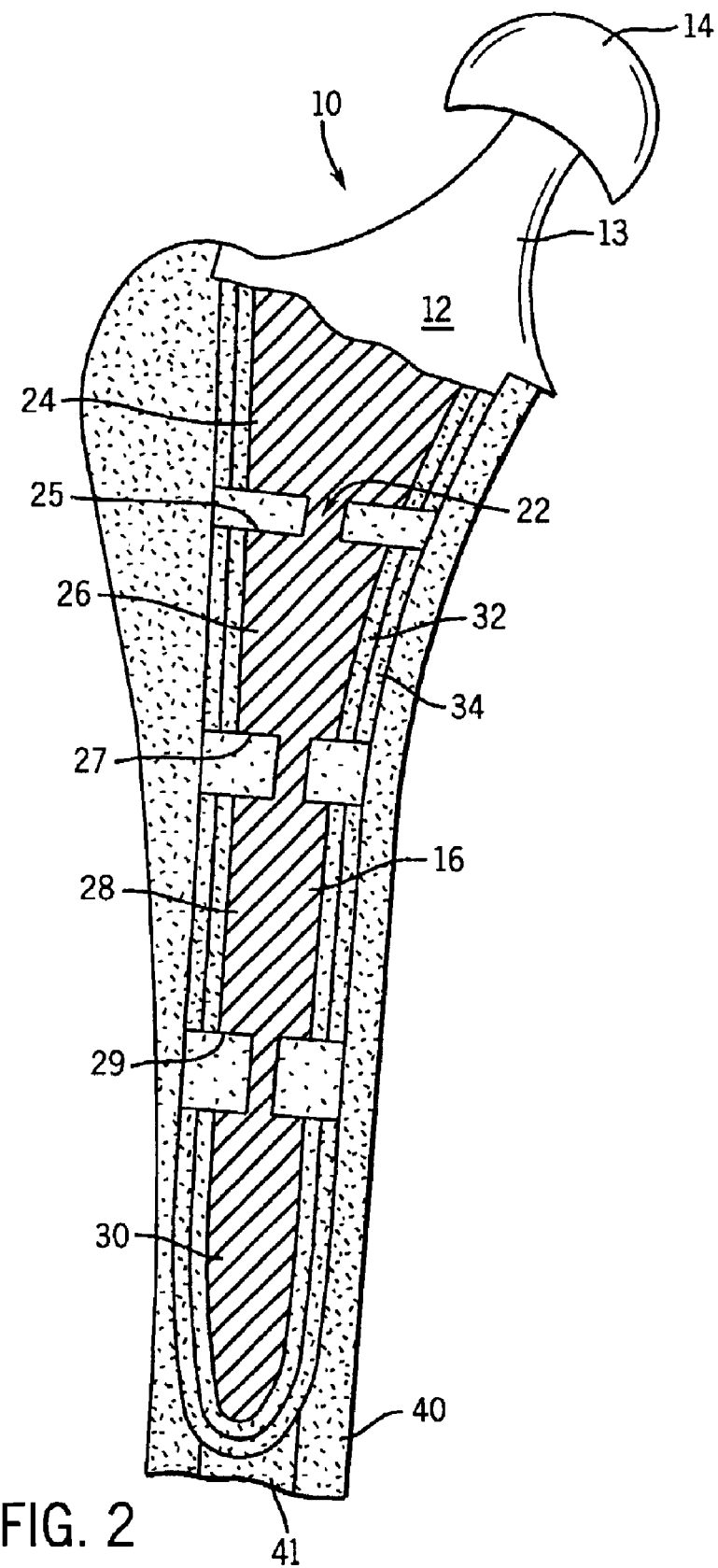
FIG. 2 is a side view similar to FIG. 1 with the prosthesis according to the invention also being shown in cross-section.

Looking at FIGS. 1 and 2, the stem 16 comprises an elongated approximately cylindrical core 22 and a plurality of approximately tubular segments 24, 26, 28 and 30 that extend outward from the core 22. The segments 24 and 26 are spaced apart so as to define a transverse groove 25 surrounding the core 22 between adjacent segments 24 and 26. The segments 26 and 28 are spaced apart so as to define a transverse groove 27 surrounding the core 22 between adjacent segments 26 and 28. The segments 28 and 30 are spaced apart so as to define a transverse groove 29 surrounding the core 22 between adjacent segments 28 and 30. While four segments have been shown for illustrative purposes, any configuration with two or more segments is possible.

In the embodiment of the prosthesis 10 shown in FIGS. 1 and 2, the core 22 and the segments 24, 26, 28 and 30 consist essentially of a microstructurally consistent implant material. A microstructurally consistent material can be formed by casting the core 22 and the segments 24, 26, 28 as a unitary piece, such as by investment casting, or by casting the stem 16 and machining out the transverse grooves 25, 27 and 29. A microstructurally consistent material typically cannot be produced by forming the core 22 and the segments 24, 26, 28 as separate pieces and thereafter securing the segments 24, 26, 28 to the core 22 by a process such as welding. Under these assembly steps, a weld line will be formed between the core 22 and the segments 24, 26, 28 such that the material is not microstructurally consistent.

The implant material used to form the core 22 and the segments 24, 26, 28 and 30 may be a metal alloy such as a titanium alloy (e.g., titanium-6-aluminum-4-vanadium), a cobalt alloy (e.g., a cobalt-chromium-molybdenum alloy), a stainless steel alloy (e.g., 316L stainless steel) or a tantalum alloy (e.g., a tantalum −10% tungsten alloy); a nonresorbable ceramic (e.g., aluminum oxide or zirconia); a nonresorbable polymeric material (e.g., ultra high molecular weight polyethylene); or a nonresorbable composite material such as a carbon fiber-reinforced polymer (e.g., carbon fiber reinforced polyethylene). Preferably, the core 22 and the segments 24, 26, 28 and 30 are formed from a metal alloy, and most preferably, are formed from a titanium alloy.

In the embodiment of the prosthesis 10 shown in FIGS. 1 and 2, the longitudinal length of each segment 24, 26, 28 and 30 is greater than the longitudinal length of each and every groove 25, 27 and 29. It can also be seen that the longitudinal length of the transverse grooves 25, 27 and 29 varies. In the embodiment shown, the transverse groove 29 has a longitudinal length greater than the longitudinal length of the transverse groove 27, which in turn has a longitudinal length greater than the longitudinal length of the transverse groove 25. Alternatively, the longitudinal length of each transverse groove 25, 27 and 29 may be the same.

The segments 24, 26, 28 and 30 may include an outer layer 32 comprising a porous material. Optionally, the entire segment may comprise a porous material. The porous material may be a porous metallic material having a network of interconnected pores distributed throughout particles of the metallic material. The particle size of the metallic particles is chosen to ensure that the resulting interstitial pore size is at least sufficient to permit bone tissue to grow into the porous material for incorporation of the femoral prosthesis 10 into the femur 40. Preferably, the metallic particles are formed from titanium, titanium alloys, cobalt alloys, stainless steel alloys, tantalum alloys, and mixtures thereof. Various methods are known for forming the outer layer 32 of porous material on the segments 24, 26, 28 and 30, such as the methods described in U.S. Pat. Nos. 5,734,959, 4,206,516 and 3,855,638. The outer layer 32 of the segments 24, 26, 28 and 30 may also include a textured surface comprising a plurality depressions such as dimples or the like. Further, the outer layer 32 of the segments 24, 26, 28 and 30 may also have a coating 34 of a bone ingrowth promoting material such as hydroxyapatite ($Ca_{10}(PO_4)_6OH_2$), a calcium phosphate (e.g., tricalcium phosphate ($Ca_3(PO_4)_2$)), growth factors, bone morphogenic proteins, and mixtures thereof. When the stem 16 having the outer layer 32 is implanted in the intramedullary canal 41 of the femur 40, the outer layer 32 of the stem 16 at least partially contacts an inner surface of the intramedullary canal 41 of the femur 40.

The prosthesis 10 may be implanted in a femur 40 as follows. First, the intramedullary canal 41 of the femur 40 is inspected and tools (such as a reamer) may be used to clean material out of the intramedullary canal 41. Once the intramedullary canal 41 of the femur 40 has been prepared, the surgeon can then "press-fit" the stem 16 of the femoral implant prosthesis 10 into the intramedullary canal 41 of the femur 40.

When implanted in a femur 40, the prosthesis 10 provides several advantages over other known implants. Looking again at FIGS. 1 and 2, it can be seen that the longitudinal length of the transverse grooves 25, 27 and 29 varies, that is, the longitudinal length of each groove increases from the proximal end 18 to the distal end 20 of the stem 16. With this arrangement of the transverse grooves 25, 27 and 29, the stiffness of the stem 16 varies by decreasing from the proximal end 18 to the distal end 20 of the stem 16. Advantageously, the rate of decrease in the stiffness from the proximal end 18 to the distal end 20 of the stem 16 can be adjusted by varying the spacing between adjacent segments. Preferably, at least one transverse groove located in a lower half of the stem has a longitudinal length greater than the longitudinal length of at least one groove located in an upper half of the stem. A larger spacing serves to more greatly reduce stem stiffness whereas a smaller spacing serves to less greatly reduce stem stiffness.

Because the distal end 20 of the stem 16 is less stiff, the distal end 20 of the stem 16 bears less force when loaded and thereby transfers more load to the proximal end 18 of the stem 16 (which has a higher stiffness). As a result, "stress shielding", in which the load bypasses or "unloads" the proximal end 18 of the stem 16, is minimized and bone resorption adjacent the proximal end 18 of the stem 16 is decreased. By adjusting the spacing between the segments and the number of segments, various stress transfer characteristics can be achieved. At the same time, sufficient surface area is provided on the outer layer 32 of the segments 24, 26, 28 and 30 such that the ingrowth of bone tissue is not materially hindered thereby decreasing the possibility of the prosthesis 10 loosening. One factor providing for sufficient bone ingrowth surface area is the absence of a longitudinal slot in the segment 30 and in particular near the lowermost end 21 of the stem 16. Another factor providing for sufficient bone ingrowth surface area is that the longitudinal length of each segment 24, 26, 28 and 30 is greater than the longitudinal length of each and every groove 25, 27 and 29.

Figure 3:
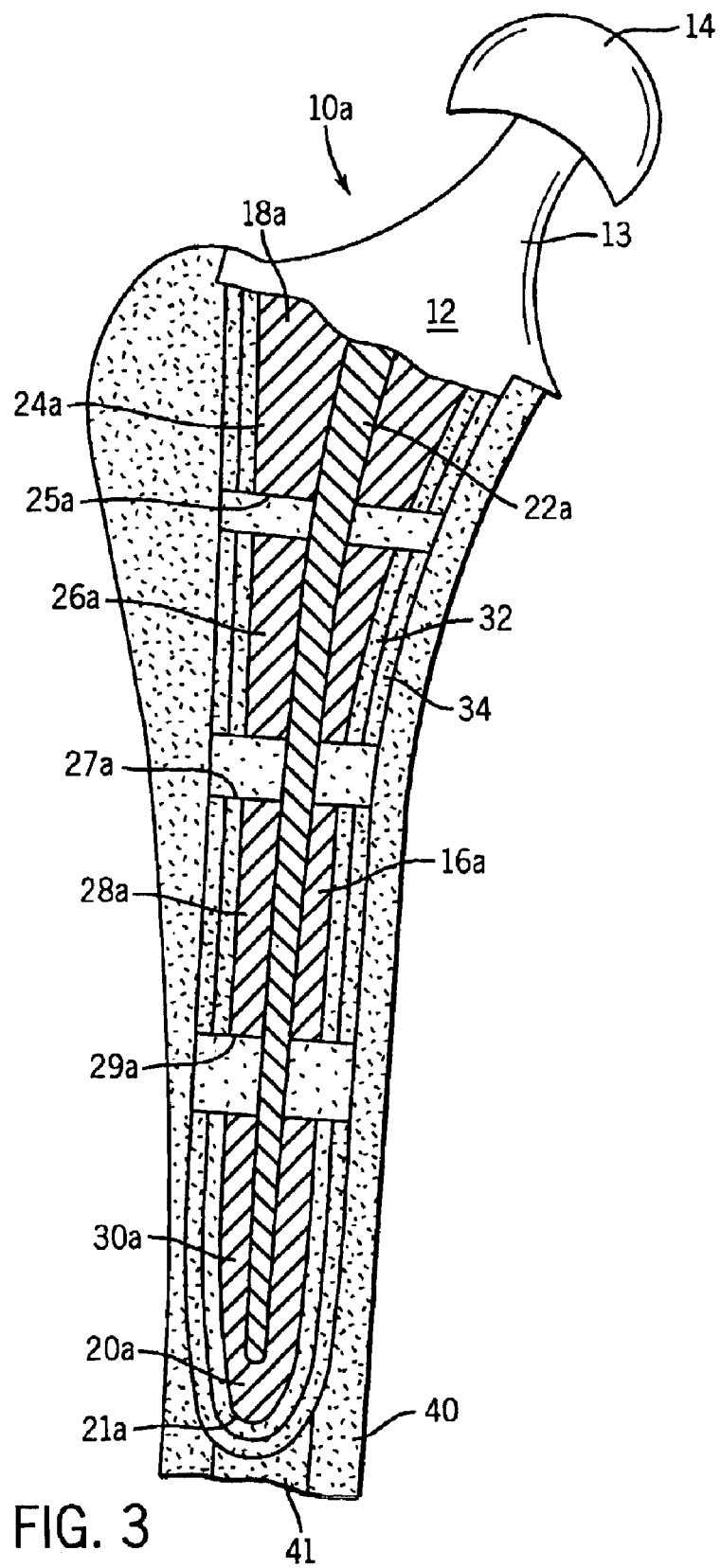
FIG. 3 is a side view similar to FIG. 1 of another prosthesis according to the invention with the prosthesis and the femur being shown in cross-section.

Turning now to FIG. 3, there is shown a second embodiment of a prosthesis 10a according to the invention. The stem 16a comprises an elongated approximately cylindrical core 22a and a plurality of approximately tubular segments 24a, 26a, 28a and 30a that are affixed to and extend outward from the core 22a. The segments 24a and 26a are spaced apart so as to define a transverse groove 25a surrounding the core 22a between adjacent segments 24a and 26a. The segments 26a and 28a are spaced apart so as to define a transverse groove 27a surrounding the core 22a between adjacent segments 26a and 28a. The segments 28a and 30a are spaced apart so as to define a transverse groove 29a surrounding the core 22a between adjacent segments 28a and 30a. While four segments have been shown for illustrative purposes, any configuration with two or more segments is possible.

In the embodiment of the prosthesis 10a shown in FIG. 3, the core 22a and the segments 24a, 26a, 28a and 30a may be formed from a metal alloy such as a titanium alloy (e.g., titanium-6-aluminum-4-vanadium), a cobalt alloy (e.g., a cobalt-chromium-molybdenum alloy), a stainless steel alloy (e.g., 316L stainless steel) or a tantalum alloy (e.g., a tantalum −10% tungsten alloy); a nonresorbable ceramic (e.g., aluminum oxide or zirconia); a nonresorbable polymeric material (e.g., ultra high molecular weight polyethylene); or a nonresorbable composite material such as a carbon fiber-reinforced polymer (e.g., carbon fiber reinforced polyethylene). Preferably, the core 22a and the segments 24a, 26a, 28a and 30a are formed from a metal alloy, and most preferably, the core 22a is formed from a titanium alloy and the segments 24a, 26a, 28a and 30a are formed from a tantalum alloy. The core 22a and the segments 24a, 26a, 28a and 30a may be assembled together using conventional techniques known to those in the art such as welding.

In the embodiment of the prosthesis 10a shown in FIG. 3, the longitudinal length of each segment 24a, 26a, 28a and 30a is greater than the longitudinal length of each and every groove 25a, 27a and 29a. It can also be seen that the longitudinal length of the transverse grooves 25a, 27a and 29a varies. In the embodiment shown, the transverse groove 29a has a longitudinal length greater than the longitudinal length of the transverse groove 27a, which in turn has a longitudinal length greater than the longitudinal length of the transverse groove 25a. Alternatively, the longitudinal length of each transverse groove 25a, 27a and 29a may be the same.

The segments 24a, 26a, 28a and 30a may include an outer layer 32 comprising a porous material. Optionally, the entire segment may comprise a porous material. The porous material may be a porous metallic material having a network of interconnected pores distributed throughout particles of the metallic material. The particle size of the metallic particles is chosen to ensure that the resulting interstitial pore size is at least sufficient to permit bone tissue to grow into the porous material for incorporation of the femoral prosthesis 10a into the femur 40. Preferably, the metallic particles are formed from titanium, titanium alloys, cobalt alloys, stainless steel alloys, tantalum alloys, and mixtures thereof. Various methods are known for forming the outer layer 32 of porous material on the segments 24a, 26a, 28a and 30a, such as the methods described in U.S. Pat. Nos. 5,734,959, 4,206,516 and 3,855,638. The outer layer 32 of the segments 24a, 26a, 28a and 30a may also include a textured surface comprising a plurality depressions such as dimples or the like. Further, the outer layer 32 of the segments 24a, 26a, 28a and 30a may also have a coating 34 of a bone ingrowth promoting material such as hydroxyapatite ($Ca_{10}(PO_4)_6OH_2$), a calcium phosphate (e.g., tricalcium phosphate ($Ca_3(PO_4)_2$)), growth factors, bone morphogenic proteins, and mixtures thereof. When the stem 16a having the outer layer 32 is implanted in the intramedullary canal 41 of the femur 40, the outer layer 32 of the stem 16a at least partially contacts an inner surface of the intramedullary canal 41 of the femur 40.

The prosthesis 10a may be implanted in a femur 40 as follows. First, the intramedullary canal 41 of the femur 40 is inspected and tools (such as a reamer) may be used to clean material out of the intramedullary canal 41. Once the intramedullary canal 41 of the femur 40 has been prepared, the surgeon can then "press-fit" the stem 16a of the femoral implant prosthesis 10a into the intramedullary canal 41 of the femur 40.

By using various combinations of materials for the core 22a and the segments 24a, 26a, 28a and 30a, the stiffness of the stem 16a can be reduced and/or varied along the longitudinal length of the stem 16a. In one version of the invention of FIG. 3, the segments 24a, 26a, 28a and 30a are formed from a first metallic material having a first modulus of elasticity (e.g., a tantalum alloy with a modulus of elasticity of approximately $27 \times 10^6$ psi.) and the core 22a is formed from a second metallic material having a second modulus of elasticity (e.g., a titanium alloy with a modulus of elasticity of approximately $16 \times 10^6$ psi.). When the first modulus of elasticity for the segment material is greater than the second modulus of elasticity for the core material, the stiffness of the stem varies at locations from the proximal end to the distal end of the stem. By varying the selection of the core and segment materials, various stress transfer characteristics can be achieved in the stem 16a.

In another version of the invention of FIG. 3, the segments 24a and 26a are formed from a first metallic material having a first modulus of elasticity (e.g., a stainless steel alloy with a modulus of elasticity of approximately $29 \times 10^6$ psi.), the segments 28a and 30a are formed from a second metallic material having a second modulus of elasticity (e.g., a tantalum alloy with a modulus of elasticity of approximately $27 \times 10^6$ psi.) and the core 22a is formed from a third metallic material having a third modulus of elasticity (e.g., a titanium alloy with a modulus of elasticity of approximately $16 \times 10^6$ psi.). Because in this arrangement the distal end 20a of the stem 16a is less stiff than the proximal end 18a of the stem 16a (i.e., the distal end 20a includes segments 28a and 30a formed from a material with a lower modulus of elasticity), the distal end 20a of the stem 16a bears less force when loaded and thereby transfers more load to the proximal end 18a of the stem 16a (which has a higher stiffness by way of the segments 24a and 26a formed from a material with a higher modulus). As a result, "stress shielding", in which the load bypasses or "unloads" the proximal end 18a of the stem 16a, is minimized and bone resorption adjacent the proximal end 18a of the stem 16a is decreased. By adjusting the spacing between the segments, the number of segments, and the,composition of the core and the segments, various stress transfer characteristics can be achieved for the stem 16a.

At the same time, sufficient surface area is provided on the outer layer 32 of the segments 24a, 26a, 28a and 30a such that the ingrowth of bone tissue is not materially hindered thereby decreasing the possibility of the prosthesis 10a loosening. One factor providing for sufficient bone ingrowth surface area is the absence of a longitudinal slot in the segment 30a and in particular near the lowermost end 21a of the stem 16a. Another factor providing for sufficient bone ingrowth surface area is that the longitudinal length of each segment 24a, 26a, 28a and 30a is greater than the longitudinal length of each and every groove 25a, 27a and 29a.

While the implantation of the femoral implant into the intramedullary canal of the femur has been illustrated and described herein, one skilled in the art will appreciate that the present invention can be practiced by other than the described embodiments, which have been presented for purposes of illustration and not of limitation. For instance, the methods and prostheses according to the invention can be used as part of the repair of other joints such as the shoulder, knee, spine, or elbow. Accordingly, the scope of the appended claims should not be limited to the description of the embodiments contained herein.

What is claimed is:

1. A prosthesis for implanting into a bone having a cavity, the prosthesis comprising:

a body; and a stem fastened to the body at a proximal end and extending longitudinally away from the body to form a distal end, the stem comprising an elongated core and a plurality of segments extending outward from the core, the core and the segments consisting essentially of a microstructurally consistent implant material, the stem having an outer layer that at least partially contacts an inner surface of the cavity of the bone when the prosthesis is implanted into the cavity of the bone, the segments being spaced apart so as to define a transverse groove surrounding the core between adjacent segments, the longitudinal length of at least one segment being greater than the longitudinal length of each groove, wherein the longitudinal length of at least two transverse grooves varies such that the stiffness of the stem varies from the proximal end to the distal end of the stem.

2. The prosthesis of claim 1 wherein:

the outer layer of the stem has pores of a size sufficient to permit bone tissue to grow into the outer layer.

3. The prosthesis of claim 2 wherein:

the outer layer of the stem comprises interconnected metallic particles that define the pores, the metallic particles comprising titanium alloys, cobalt alloys, stainless steel alloys, tantalum alloys, or mixtures thereof.

4. The prosthesis of claim 1 wherein:

the implant material is selected from titanium alloys, cobalt alloys, stainless steel alloys, and tantalum alloys.

5. The prosthesis of claim 1 wherein:

the outer layer of the stem has a coating of a bone ingrowth promoting material selected from hydroxyapatite, calcium phosphates, growth factors, bone morphogenic proteins, and mixtures thereof.

6. The prosthesis of claim 1 wherein:

the prosthesis is a femoral prosthesis.

7. The prosthesis of claim 1 wherein:

the longitudinal length of the transverse grooves increases from a first groove near the proximal end of the stem to a last groove near the distal end of the stem.

8. The prosthesis of claim 1 wherein:

at least one transverse groove located in a lower half of the stem has a longitudinal length greater than the longitudinal length of at least one groove located in an upper half of the stem.

* * * * *